US00PP09235P

United States Patent [19]

Okudai et al.

[11] Patent Number: Plant 9,235

[45] Date of Patent: Aug. 8, 1995

[54] CITRUS TREE 'ARIAKE'

[75] Inventors: Naomi Okudai, Arita; Iwao Oiyama, Tokyo; Ryoji Matsumoto, Chikushino; Toshio Takahara; Masashi Yamamoto, both of Minamitakaki; Denji Ishiuchi, Mie; Kensuke Asada, Omura; Hidekazu Ikemiya, Okinawa; Hirono Murata, Aomori; Yoshio Yamada, Nagasaki, all of Japan

[73] Assignee: Fruit Tree Research Station, Ministry of Agriculture, Forestry and Fisheries, Tsukuba, Japan

[21] Appl. No.: 214,167

[22] Filed: Mar. 16, 1994

[51] Int. Cl.[6] ..... A01H 5/00

[52] U.S. Cl. ..... Plt./45

[58] Field of Search ..... Plt. 45

[56] References Cited

PUBLICATIONS

Journal of Fruit Tree, Seed and Seedling "Explanation fo the Newly-registered Variety".

Journal of Fruit Japan "Technology for Breeding a New Variety".

Journal of Japan Society of Horticulture "New Citrus Variety 'Ariake'".

Journal of New Technology of Kyushu Agriculture "Breeding of the New Citrus Variety 'Ariake'".

*Primary Examiner*—James R. Feyrer

*Attorney, Agent, or Firm*—Armstrong, Westerman, Hattori, McLeland & Naughton

[57] ABSTRACT

Disclosed is a citrus tree having a moderate spreading vigor, and bearing medium size and compressed round shaped fruit with a deep orange skin color and a low acidity. This new and distinct variety of citrus tree is an early maturing citrus cultivar, is fairly resistant to diseases, was bred by a crossing of "Seike navel" (the seed parent) and "Clementine" (the pollen parent), bears good quality fruit, and is an excellent citrus cultivar.

5 Drawing Sheets

BACKGROUND OF THE VARIETY

The present invention relates to a new and distinct variety of citrus tree, and more particularly, to a citrus tree having a strong resistance to diseases compared with Navel Orange and a low acidity, and bearing an excellent table fruit.

In Japan, the variety "Navel Orange", which is an early maturing cultivar, has been cultured, to provide a table fruit, but the fruit of this variety may have a high acidity at the end of year marketing season and a weak resistance to diseases, and there is a continuing need for a citrus variety having a higher quality as a table fruit than the conventional variety.

The efforts by the present breeders have been aimed at obtaining a new variety that can replace "Navel Orange". Namely, the object of the present invention is to provide a new and distinct variety of citrus tree bearing a fruit of high quuality, having a strong resistance to diseases annd a low acidity, having no seeds, and ripening in early season.

ORIGIN AND ASEXUAL REPRODUCTION OF THE VARIETY

This new variety of citrus tree was a cross-seedling obtained from a crossing of "Seike navel" (♀) (the seed parent) and "Clementine" (♂) (the pollen parent) at the Kuchinotsu Branch, Fruit Tree Research Station (Otsu-870, Kuchinotsu-cho, Minamitakaki-gun, Nagasaki-ken, Japan).

Specially, this crossing was carried out at the Kuchinotsu Branch in 1973, and in 1974 the resulting seeds were sown in a glass house to grow seedlings. The scion obtained from the seedlings were top-worked to a *Citrus unshiu* Marc. for interstock, to shorten the juvenile phase, in September, 1974, and the tree thus— grown bore fruit for the first time in 1978; and the quality of the fruit met the above-mentioned purpose. Accordingly, the tree was selected as the first selection based on the results of a few years' research, and was subjected to local adaptability tests, beginning in 1987. These tests were conducted at 21 of the experimental stations in the main Japanese citrus-growing regions such as Nagasaki-ken, and Wakayama-ken, etc., under the strain number "Kuchinotsu 13".

As a result, it was found that the trees had stable characteristics, and can be disyinguished from other similar varieties. The breeders denominated the afore-said citrus variety of tree in accordance with this invention as "Ariake". The genus of the cultivate is "Citrus", and the group of the same is "Tangor (hybrid of mandarin and sweet orange)".

The afore-said variety "Seike navel" is the seed parent and is an early maturing citrus that is used as a body to breed seedless variety, and bears fruit with a high productivity and a high quality. Another variety "Clementine" bears fruit with a low acidity, a high Brix, and a relatively strong resistance to diseases.

The breeders asexually reproduced this new and distinct variety of citrus tree "Ariake", by grafting, at the Kuchinotsu Branch, and at other Branches of the Fruit Tree Research Station, Ministry of Agriculture, Forestry and Fisheries, Japan, and confirmed the homogeneity and stability of "Ariake" according to this invention.

An application for this new variety of citrus tree "Ariake" under the Seeds and Seedlings Law of Japan was filed on Apr. 30, 1992, and was registered on Jul. 17, 1992 under the registration number 4.

SUMMARY OF THE VARIETY

This new variety of citrus tree has a moderate vigor with a growth habit of spreading, and an internode with a moderate thickness and length. There are few thorns on the tree, and the shape of the leaf of the tree is fusiform and similar in appearance to "Seike navel". The size of the leaf is smaller than that of "Clementine", and is slightly larger than that of "Seike navel". The flower is raceme, and is smaller than that of "Seike navel", but is larger than that of "Clementine". The color of the flower is white, and it has 4.7 petals. The fertility of the pollen is low, and the female sterility is very high, and the fruit is almost seedless. The bearing age and fruit set percentage of the tree are medium.

The fruit generally has a weight of about 154g; this is bigger than that of "Clementine", but is smaller than that of "Seike navel". The shape of the fruit is round and the skin of the fruit has a deeper orange-color, similar to "Seike navel", and the optimum color of the fruit is reached in early December. The surface of the fruit is smooth and the thickness of the skin is 3.9 mm, and the peeling characteristic is slightly inferior to that of "Clementine". The flesh is deep orange colored, and similar to "Clementine". The texture of the flesh is soft and juicy, and similar to "Clementine". Further, the flesh has a high sweetness, a low acidity, and moderate flavor. The segments of the flesh are thin. The embryo is white colored, and is monoembryo.

Regarding damage by diseases, the tree of this invention has a strong resistance to scab, and a normal or slightly strong resistance to bacterial canker. Further, the tree of this variety has a fairly and moderately resistance to cold.

The color values presented herein are taken from the Inter-Society Color Council-National Bureau of Standards (ISCC-NBC).

DESCRIPTION OF THE VARIETY

Figure 1:
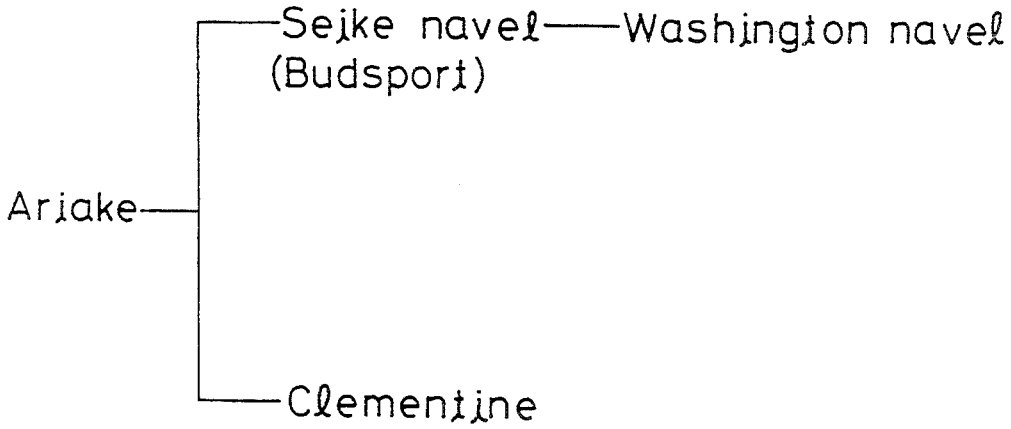
FIG. 1 gives the pedigree of the new and distinct variety of the citrus tree "Ariake"
Figure 2:
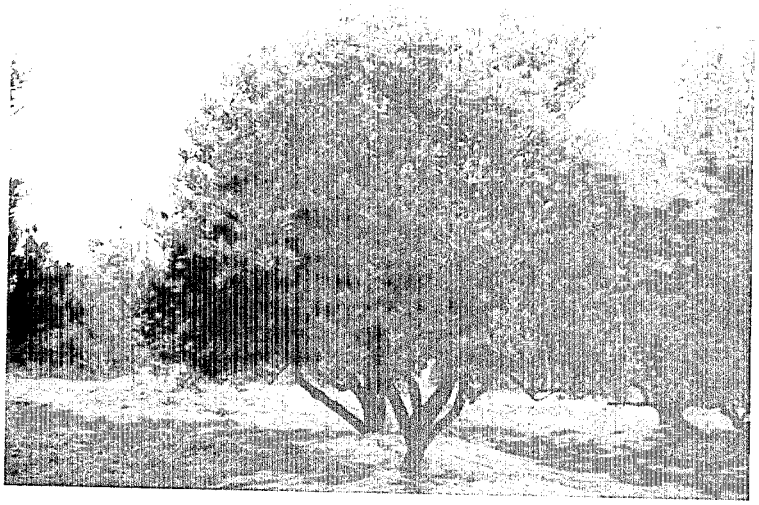
FIG. 2 is a photograph of a shape of the new variety of citrus tree.
Figure 3:
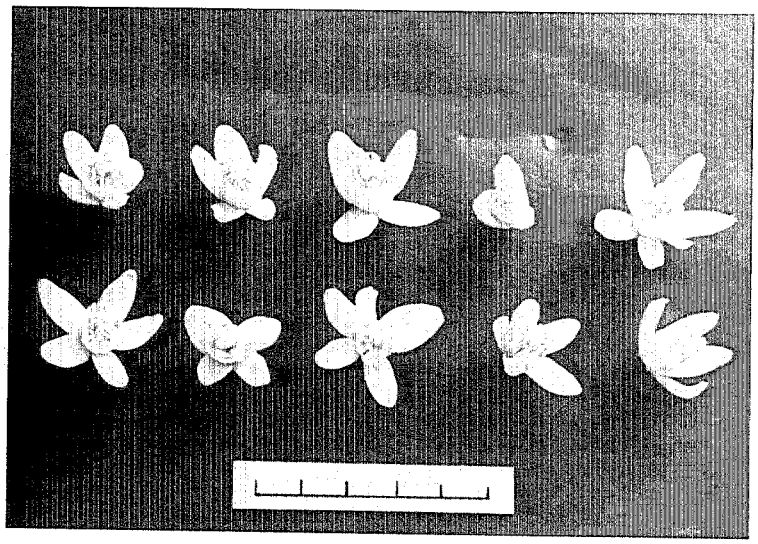
FIG. 3 is a photograph of the flowers of the new variety of citrus tree.
Figure 4:
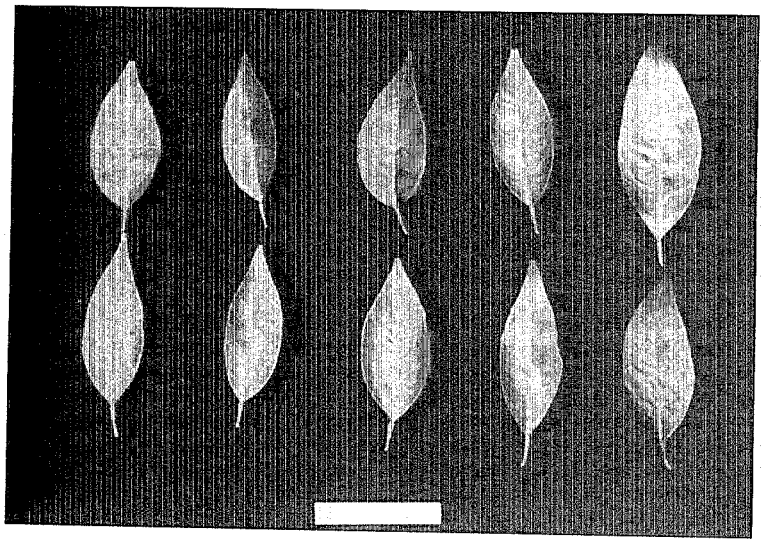
FIG. 4 is a photograph of adult leaves (upper and reverse side) of the new variety of citrus tree.
Figure 5:
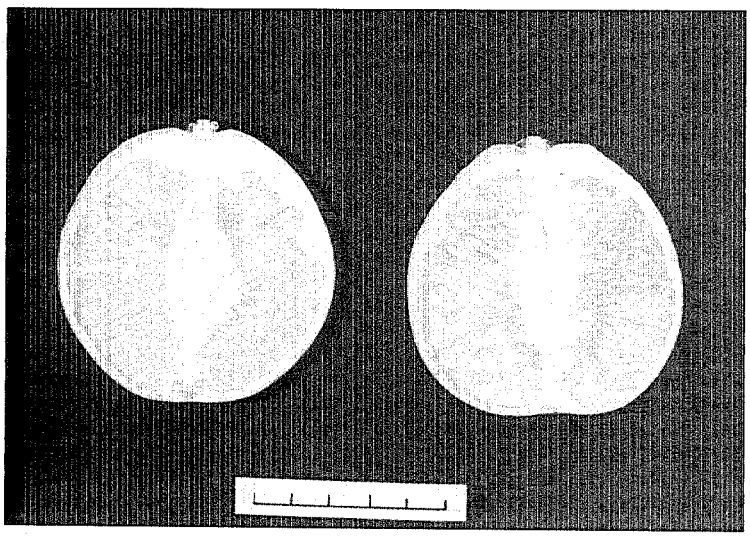
FIG. 5 is a photograph of longitudinal-sectional views of the fruit of the new variety of citrus tree.
Figure 6:
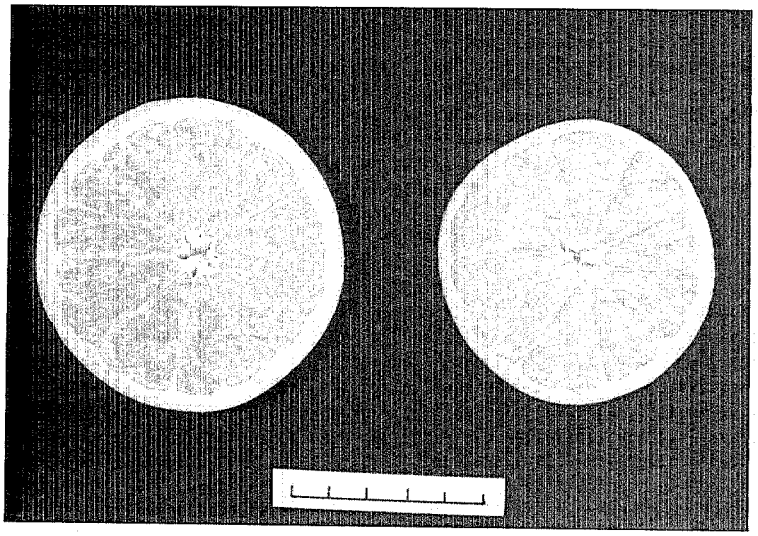
FIG. 6 is a photograph of cross-sectional views of the fruit of the new variety of citrus tree.
Figure 7:
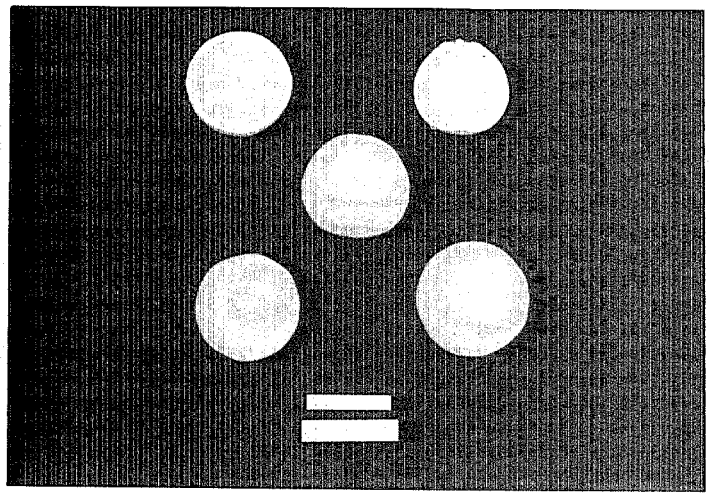
FIG. 7 is a photograph of a side view (in the middle), from the blossom end (lower row, right-hand) and from the stem end (and from the stem end (lower row, left-hand) of the fruit of the new variety of citrus tree.

The characteristics of the new and distinct variety of citrus tree "Ariake" are as follows:

Ploidy: Diploid, as both parents are. Note: Near seedlessness is due to low female sterility and low seed formation.

Tree and branch:

*Habit of branches.*—Upright.

*Size of tree.*—Medium.

*Vigor.*—Weak. Tree is dwarf, with canopy size equal to $\frac{1}{2}$ to $\frac{3}{4}$ the canopy size of orange trees.

*Thickness of shoot.*—Medium.

*Length of internode*—Medium.

*Number of prickles on shoot.*—Few.

Pruning and training carried out in Japan to provide significant sunlight to branches and raise productivity. (Abbreviations used hereinafter are as follows: "Seike navel" (S) "Clementine" (C)).

Leaf:

*Leaf blade shape index.*—Low, 2.49% (S: 2.40%, C: 2.79%).

*Angle of leaf blade apex.*—Moderate, 36.6 ° (S: 40.2°, C: 32.3°).

*Angle of leaf blade base.*—Moderate, 53.0° (S: 51.4°, C: 49.8°).

*Thickness of leaf blade.*—Thin, 0.42 mm (S: 0.42 mm. C: 0.33 mm).

*Area of leaf blade.*—Small, 17.2 $cm^2$ (S: 15.9 $cm^2$, C: 22.2 $cm^2$).

*Length of leaf blade.*—Short, 7.9 cm (S: 7.4 cm. C: 9.5 cm).

*Width of leaf blade.*—Medium, 3.2 cm (S: 3.1 cm, C: 3.4 cm).

*Sharpness of vein.*—Unclear, same as "S" and "C".

*Shape of wings.*—2.93 (S: 2.63, C: 3.00).

*Length of petiole.*—Medium, 1.1 cm (S: 1.3 cm, C: 1.2 cm).

*Rate of petiole.*—13.9% (S: 17.6%, C: 12.6%).

Flower:

*Date of blooming.*—May 8.

*Formation of inflorescence.*—Raceme, same as "S", C: Solitary.

*Weight of flower bud.*—Medium, 0.57 g (S: 0.72 g, C: 0.28 g).

*Shape of petal apex.*—Sharp, S: Sharp, C: Sharp.

*Shape of petal base.*—Flat, S: Flat, C: Flat.

*Length of petal.*—Long, 15 mm (S: 16 mm, C: 12 mm).

*Color of petal.*—White (ISCC-NBC yellowish white), same as "S" and "C".

*Number of petals.*—Few, 4.7 (S: 4.6, C: 4.8).

*Degree of separation of filament.*—Separative, (S: Only base fuses, C: Separative).

*Fertility of pollen.*—Few, same as "C", S: Sterile.

*Size of ovary.*—Small, 2.9 mm in diameter (S: 4.1 mm, C: 2.4 mm).

Fruit:

*Yield.*—2–3 tons/300 trees/100×100 $m^2$.

*Shape of fruit.*—Compressed round (S: Round, C: Flat).

*Shape of fruit stylar end.*—Flat (S: Round, C: Concave).

*Depth of navel.*—0.5 cm, (S: 4.1 cm, C: 0.0 cm).

*Size of stylar scar.*—Small, 1.8 mm (S: Navel, C: 1.5 mm).

*Shape of basal end.*—Flat (S: Flat, C: Slightly concave).

*Number of radially corrugated fruit on peduncle.*—Many (S: Few, C: Few).

*Size of columella in cross section.*—Small, 3.1% (S: 2.1%, C: 1.5%).

*Size of fruit.*—Medium, mean weight of 154 g; range of 99–230 g. (S: 256 g, C: 96 g).

*Uniformity of fruit size.*—Medium; Index of fruit shape [horizontal diameter/vertical diameter)×100]=mean value of 107 (range of 100–111).

*Fruit shape.*—Spheroid.

*Color of overskin.*—Orange to deep orange (ISCC-NBC Vivid Orange).
*Size of oil glands.*—Medium (S: Medium, C: Large).
*Type of skin surface.*—Smooth, same as "C"; easily peeled; S: Medium.
*Density of oil glands.*—Dense, 99.4 oil glands/$cm^2$ (S: 57.4.g./$cm^2$, C: 58.8.g./$cm^2$).
*Irregularity of oil glands.*—Flat (S: Convex).
*Number of dents.*—None.
*Thickness of peel.*—Thin, 3.9 mm (S: 4.2 mm, C: 2.2 mm).
*Hardness of peeling.*—Moderate, easier than "S".
*Toughness of segment membrane.*—Soft (S: Medium, C: Medium).
*Flesh.*—Soft and juicy.
*Shape of juice sac.*—Spindle-shape.
*Size of juice sac.*—Large.
*Color of juice sac.*—Orange (ISCC-NBC Vivid Orange).
*Juice amount.*—Medium.
*Sweetness.*—Rich (Brix 12.0° to 12.5°).
*Acidity.*—Low.
*Number of seed.*—Rare.
*Color of embryo.*—Pale Green (ISCC-NBC Pale yellow Green).
*Number of embryo.*—Monoembryony.
*Germination time*.*—Early, March 7th.
*Flowering time*.*—Early, April 28th.

*Time of maturity of fruit*.*—Medium (Early December).
*Harvest season*.*—December 15–25. Fruit cannot be left on tree for a long time. No regreening or puffing observed since fruit harvested promptly.
*Ability of fruit to be stored.*—Lower than for "Navel Orange".
*Alternate bearing.*—Medium.
*Physiological characteristics.*—Occurrence of sunburn: Very little. Occurrence of peel puffing: Very little.
*Occurence of fruit cracking.*—Moderate.
*Resistance to disease.*—Relatively Strong.
*Resistance to pest.*—Moderate.

* in the Nagasaki prefecture district, Japan.

We claim:

1. A new and distinct variety of citrus tree, substantially as illustrated and described herein, characterized over known citrus trees by (A) having a moderate vigor with a growth habit of spreading; (B) having a medium compressed round type fruit, with a deep orange skin color, and a smooth skin;

wherein said fruit is moderately peeled; and the flesh of the fruit has a soft texture, a moderate orange flavor and a low acidity, is juicy and sweet; and seedless; and thus said fruit is suitable as table fruit; (C) having a relatively strong resistance to diseases.

* * * * *

Pedigree of 'Ariake'